US008785388B2

(12) United States Patent
Perlman

(10) Patent No.: US 8,785,388 B2
(45) Date of Patent: Jul. 22, 2014

(54) TAT-BH3 METHODS FOR TREATING ARTHRITIS

(75) Inventor: Harris R. Perlman, St. Louis, MO (US)

(73) Assignee: Saint Louis University, St. Louis, MO (US)

(*) Notice: Subject to any disclaimer, the term of this patent is extended or adjusted under 35 U.S.C. 154(b) by 0 days.

(21) Appl. No.: 12/031,118

(22) Filed: Feb. 14, 2008

(65) Prior Publication Data

US 2008/0234178 A1     Sep. 25, 2008

Related U.S. Application Data

(60) Provisional application No. 60/901,591, filed on Feb. 14, 2007.

(51) Int. Cl.
| *A61K 38/16* | (2006.01) |
| *C07K 19/00* | (2006.01) |
| *C07K 14/47* | (2006.01) |
| *C07K 7/00* | (2006.01) |

(52) U.S. Cl.
USPC ......... 514/16.6; 514/18.9; 514/1.2; 514/21.3; 530/402

(58) Field of Classification Search
None
See application file for complete search history.

(56) References Cited

U.S. PATENT DOCUMENTS 5,998,583 A * 12/1999 Korsmeyer
2008/0274956 A1 * 11/2008 Bonny et al.

FOREIGN PATENT DOCUMENTS

EP     1661912 A1 * 5/2006

OTHER PUBLICATIONS

Hutchenson et al., The BH3 pro-apoptotic gene, Bim is required to inhibit the effector phase of experimental arthritis, Arthritis Rheumatism, 52(9 Suppl S):5251, Nov. 2005.*
Pope, R.M. & Perlman, H. Rheumatoid Arthritis. in Current Molecular Medicine: Principles of Molecular Rheumatology (ed. Tsokos, G.C.) 325-361 (Copyright by Humana Press Inc., Totowa, NJ, 2000).
Matsumoto, S., Muller-Ladner, U., Gay, R.E., Nishioka, K. & Gay, S. Ultrastructural Demonstration of Apoptosis, Fas and Bcl-2 Expression of Rheumatoid Synovial Fibroblasts. The Journal of Rheumatology, vol. 23, 1345-1352 (1996).
Sugiyama, M. et al. Localization of apoptosis and expression of apoptosis related proteins in the synovium of patients with rheumatoid arthritis. Annals of the Rheumatic Diseases, vol. 55, 442-449 (1996).
Liu, H. & Pope, R.M. Apoptosis in rheumatoid arthritis: friend or foe. Rheumatic Disease Clinics of North America vol. 30, 603-25, (Copyright by Elsevier, Inc., 2004).
Adams, J.M. & Cory, S. The Bcl-2 Protein Family: Arbiters of Cell Survival. Science vol. 281, 1322-1326 (Copyright by American Associate for the Advancement of Science, Washington, DC, 1998).

(Continued)

*Primary Examiner* — Claire Kaufman
(74) *Attorney, Agent, or Firm* — Mark E. Stallion, Esq.; Husch Blackwell LLP

(57) ABSTRACT

The present invention is directed to compositions and methods for treating immune system mediated disease. In particular, certain embodiments of the present invention use BH3 mimetic therapy as an efficacious treatment of the effector phase of RA wherein the compositions and methods of the present invention markedly reduce the level of the Bcl-2 antagonist protein Bim present in RA synovial tissue as compared to control patients. Therefore, the present invention involves restoring the function of Bim in order to ameliorate inflammatory arthritis. In connection therewith, systemic delivery of a peptide to the BH3 domain of Bim effectively inhibits the development of K/BxN serum transfer-induced arthritis which closely resembles the effector phase of RA.

9 Claims, 6 Drawing Sheets

(56) References Cited

OTHER PUBLICATIONS

Kroemer, G. The proto-oncogene Bcl-2 and its role in regulating apoptosis. Nature Medicine vol. 3, No. 6, 614-620 (Copyright by Nature Publishing Group, Jun. 1997).
Opferman, J.T. & Korsmeyer, S.J. Apoptosis in the development and maintenance of the immune system. Nature Immunology, vol. 4, No. 5, 410-5 (Copyright by Nature Publishing Group, May 2003).
Green, D.R. & Reed, J.C. Mitochondria and Apoptosis. Science vol. 281, 1309-1312 (Copyright by the American Association for the Advancement of Science, Washington, DC, 1998).
Zamzami, N., Brenner, C., Marzo, I., Susin, S.A. & Kroemer, G. Subcellular and submitochondrial mode of action of Bcl-2-like oncoproteins. Oncogene vol. 16, 2265-2282 (Copyright by Stockton Press, 1998).
Yang, J. et al. Prevention of apoptosis by Bcl-2: Release of cytochrome c from mitochondria blocked. Science vol. 275, 1129-1132 (Copyright by the American Association for the Advancement of Science, Washington, DC, 1997).
Kluck, R.M., Bossy-Wetzel, E., Green, D.R. & Newmeyer, D.D. The release of cytochrome c from mitochondria: A primary site for Bcl-2 regulation of apoptosis. Science vol. 275, 1132-1136 (Copyright by the American Association for the Advancement of Science, Washington, DC, 1997).
Kuida, K. et al. Reduced apoptosis and cytochrome c-mediated caspase activation in mice lacking caspase 9. Cell, vol. 94, 325-337 (Copyright by Cell Press, 1998).
Rao, L. & White, E. Bcl-2 and the ICE family of apoptotic regulators: making a connection. Current Opinion in Genetics & Development, vol. 7, 52-58 (Copyright by Current Biology Ltd., 1997).
Perlman, H. et al. Bcl-2 expression in synovial fibroblasts is essential for maintaining mitochondrial homeostasis and cell viability. The Journal of Immunology, vol. 164, 5227-5235 (Copyright by The American Association of Immunologists, 2000).
Harris, M.H. & Thompson, C.B. The role of the Bcl-2 family in the regulation of outer mitochondrial membrane permeability. Cell Death and Differentiation, vol. 7, 1182-91. (Copyright by Macmillan Publishers Ltd., 2000).
Ahsen, O.V., Waterhouse, N.J., Kuwana, T., Newmeyer, D.D. & Green, D.R. The 'harmless' release of cytochrome c. Cell Death Differentiation, vol. 7, 1192-9. (Copyright by Macmillan Publishers Ltd., 2000).
Rathmell, J.C., Lindsten, T., Zong, W.X., Cinalli, R.M. & Thompson, C.B. Deficiency in Bak and Bax perturbs thymic selection and lymphoid homeostasis. Nature Immunology, vol. 3, No. 10, 932-9 (Copyright by Nature Publishing Group, 2002).
Cheng, E.H. et al. BCL-2, BCL-X(L) sequester BH3 domain-only molecules preventing BAX- and BAK-mediated mitochondrial apoptosis. Molecular Cell, vol. 8, 705-11 (Copyright by Cell Press, 2001).
Zong, W.X., Lindsten, T., Ross, A.J., MacGregor, G.R. & Thompson, C.B. BH3-only proteins that bind pro-survival Bcl-2 family members fail to induce apoptosis in the absence of Bax and Bak. Genes & Development, vol. 15, 1481-6 (Copyright by Cold Spring Harbor Laboratory Press, 2001).
Lindsten, T. et al. The combined functions of proapoptotic Bcl-2 family members bak and bax are essential for normal development of multiple tissues. Molecular Cell, vol. 6, 1389-99 (Copyright by Cell Press, 2000).
Labi, V., Erlacher, M., Kiessling, S. & Villunger, A. BH3-only proteins in cell death initiation, malignant disease and anticancer therapy. Cell Death Differentiation, vol. 13, 1325-1338 (Copyright by Nature Publishing Group, 2006).
Letai, A. et al. Distinct BH3 domains either sensitize or activate mitochondrial apoptosis, serving as prototype cancer therapeutics. Cancer Cell, vol. 2, 183-92 (Copyright by Cell Press, 2002).
Certo, M. et al. Mitochondria primed by death signals determine cellular addiction to antiapoptotic BCL-2 family members. Cancer Cell, vol. 9, 351-65 (Copyright by Elsevier Inc., 2006).
Chen, L. et al. Differential targeting of prosurvival Bcl-2 proteins by their BH3-only ligands allows complementary apoptotic function. Molecular Cell, vol. 17, 393-403 (Copyright by Elsevier Inc., 2005).
Willis, S.N. et al. Proapoptotic Bak is sequestered by Mcl-1 and Bcl-xL, but not Bcl-2, until displaced by BH3-only proteins. Genes and Development, vol. 19, 1294-305 (Copyright by Cold Spring Harbor Laboratory Press, 2005).
Kuwana, T. et al. BH3 domains of BH3-only proteins differentially regulate Bax-mediated mitochondrial membrane permeabilization both directly and indirectly. Molecular Cell, vol. 17, 525-35 (Copyright by Elsevier Inc., 2005).
Kim, H. et al. Hierarchical regulation of mitochondrion-dependent apoptosis by BCL-2 subfamilies. Nature Cell Biology, vol. 8, No. 12, 1348-58 (Copyright by Nature Publishing Group, 2006).
Willis, S.N. et al. Apoptosis initiated when BH3 ligands engage multiple Bcl-2 homologs, not Bax or Bak. Science vol. 315, 856-9 (Copyright by the American Association for the Advancement of Science, Washington, DC, 2007).
Letai, A. Pharmacological manipulation of Bcl-2 family members to control cell death. The Journal of Clinical Investigation, vol. 115, No. 10, 2648-55 (Oct. 2005).
Goldsmith, K.C. et al. BH3 peptidomimetics potently activate apoptosis and demonstrate single agent efficacy in neuroblastoma. Oncogene, vol. 25, 4525-33 (Copyright by Nature Publishing Group, 2006).
Scatizzi, J.C., Bickel, E., Hutcheson, J., Haines, G.K., Ill & Perlman, H. Bim deficiency leads to exacerbation and prolongation of joint inflammation in experimental arthritis. Arthritis & Rheumatism, vol. 54, No. 10, 3182-93 (Copyright by American College of Rheumatology, 2006).
Dai, S., Hirayama, T., Abbas, S. & Abu-Amer, Y. The IkappaB kinase (IKK) inhibitor, NEMO-binding domain peptide, blocks osteoclastogenesis and bone erosion in inflammatory arthritis. The Journal of Biological Chemistry, vol. 279, No. 36, 37219-22 (Copyright by the Society for Biochemistry and Molecular Biology, Inc., U.S.A., 2004).
Hirayama, T., Dai, S., Abbas, S., Yamanaka, Y. & Abu-Amer, Y. Inhibition of inflammatory bone erosion by constitutively active STAT-6 through blockade of JNK and NF-kappaB activation. Arthritis & Rheumatism, vol. 52, No. 9, 2719-29 (Copyright by American College of Rheumatology, 2005).
Kashiwagi, H. et al. Tat-Bim Induces Apoptosis in Cancer Cells. Annals of Surgical Oncology, vol. 14, No. 5, (Copyright by The Society of Surgical Oncology, Inc., 2007), Published by Springer Science+Business Media, Inc.
Perlman, H. et al. Differential expression pattern of the antiapoptotic proteins, Bcl-2 and Flip in experimental arthritis. Arthritis & Rheumatism, vol. 44, No. 12, 2899-908 (Copyright by American College of Rheumatology, 2001), Published by Wiley-Liss, Inc.
Pettit, A.R. et al. TRANCE/RANKL knockout mice are protected from bone erosion in a serum transfer model of arthritis. American Journal of Pathology, vol. 159, No. 5, 1689-99 (Copyright by American Society for Investigative Pathology, 2001).
Liu, H. et al. Mcl-1 is essential for the survival of synovial fibroblasts in rheumatoid arthritis. The Journal of Immunology, vol. 1175, 8337-45 (Copyright by the American Association of Immunologists, Inc., 2005).
Busteed, S. et al. Bcl-x(L) expression in vivo in rheumatoid synovium. Clinical Rheumatology, vol. 25 (Copyright by Clinical Rheumatology, 2006).
Brown, N.J. et al. Fas death receptor signaling represses monocyte numbers and macrophage activation in vivo. The Journal of Immunology, vol. 173, 7584-93 (Copyright by The American Association of Immunologists, Inc., 2004).
Scatizzi, J.C. et al. p21Cip1 is required for the development of monocytes and their response to serum transfer-induced arthritis. American Journal of Pathology, vol. 168, No. 5, 1531-41 (Copyright by American Society for Investigative Pathology, 2006).
Solomon, S., Rajasekaran, N., Jeisy-Walder, E., Snapper, S.B. & Illges, H. A crucial role for macrophages in the pathology of K/BxN serum-induced arthritis. European Journal of Immunology, vol. 135, 3064-73 (Copyright by WILEY-VCH Verlag GmnH & Co. KGaA, Weinheim, 2005).

(56) References Cited

OTHER PUBLICATIONS

Wipke, B.T. & Allen, P.M. Essential role of neutrophils in the initiation and progression of a murine model of rheumatoid arthritis. The Journal of Immunology, vol. 167, 1601-8 (Copyright by The American Journal of Immunologists, 2001).

Kyburz, D. & Corr, M. The KRN mouse model of inflammatory arthritis. Springer Seminars in Immunopathology, vol. 25, 79-90 (Copyright by Springer-Verlag, 2003).

Salmon, M. et al. Inhibition of T cell apoptosis in the rheumatoid synovium. The Journal of Clinical Investigation, vol. 99, No. 3, 439-446 (Copyright by The American Society for Clinical Investigation, Inc., 1997).

Hilbers, I. et al. Expression of the apoptosis accelerator Bax in rheumatoid arthritis synovium. Rheumatology International, vol. 23, 75-81 (Copyright by Springer-Verlag, 2002).

Cha, H.S., Rosengren, S., Boyle, D.L. & Firestein, G.S. PUMA regulation and proapoptotic effects in fibroblast-like synoviocytes. Arthritis & Rheumatism, vol. 54, No. 2, 587-92 (Copyright by American College of Rheumatology, 2006).

Chen, M., Huang, L. & Wang, J. Deficiency of Bim in dendritic cells contributes to overactivation of lymphocytes and autoimmunity. Blood, vol. 109, No. 10, 4360-4367 (Copyright by The American Society of Hematology, Washington, DC, 2007).

Walensky, L.D. et al. Activation of apoptosis in vivo by a hydrocarbon-stapled BH3 helix. Science, vol. 305, 1466-70 (Copyright by The American Associate for the Advancement of Science, Washington, DC, 2004).

Lee, D.M. et al. Mast cells: a cellular link between autoantibodies and inflammatory arthritis. Science, vol. 297, 1689-92 (Copyright by The American Association for the Advancement of Science, Washington, DC, 2002).

Dzhagalov, I., St John, A. & He, Y.W. The antiapoptotic protein Mcl-1 is essential for the survival of neutrophils but not macrophages. Blood, vol. 109, 1620-6 (Copyright by The American Society of Hematology, Washington, DC, 2007).

Wipke, B.T., Wang, Z., Nagengast, W., Reichert, D.E. & Allen, P.M. Staging the initiation of autoantibody-induced arthritis: a critical role for immune complexes. The Journal of Immunology, vol. 172, 7694-702 (Copyright by The American Association of Immunologists, Inc., 2004).

Letai, A. Restoring cancer's death sentence. Cancer Cell, vol. 10, 343-5 (Copyright by Elsevier Inc., 2006).

Shore, G.C. & Viallet, J. Modulating the Bcl-2 family of apoptosis suppressors for potential therapeutic benefit in cancer. Hematology 2005, American Society of Hematology, 226-30 (2005).

Letai, A. & Scorrano, L. Laying the foundations of programmed cell death. Cell Death and Differentiation, vol. 13, 1245-7 (Copyright by Nature Publishing Group, 2006).

Chauhan, D. et al. A novel Bcl-2/Bcl-X(L)lBcl-w inhibitor ABT-737 as therapy in multiple myeloma. Oncogene, vol. 26, 2374-80 (Copyright by Nature Publishing Group, 2006).

Chen, S., Dai, Y., Harada, H., Dent, P. & Grant, S. Mcl-1 downregulation potentiates ABT-737 lethality by cooperatively inducing Bak activation and Bax translocation. Cancer Research, vol. 67, 782-91 (Copyright by American Association for Cancer Research, 2007).

Del Gaizo Moore, V. et al. Chronic lymphocytic leukemia requires BCL2 to sequester prodeath BIM, explaining sensitivity to BCL2 antagonist ABT-737. The Journal of Clinical Investigation, vol. 117, No. 1, 112-21 (Jan. 2007).

Konopleva, M. et al. Mechanisms of apoptosis sensitivity and resistance to the BH3 mimetic ABT-737 in acute myeloid leukemia. Cancer Cell, vol. 10, 375-88 (Copyright by Elsevier Inc., 2006).

Oltersdorf, T. et al. An inhibitor of Bcl-2 family proteins induces regression of solid tumours. Nature, vol. 435, 677-81 (Copyright by Nature Publishing Group, 2005).

Tahir, S.K. et al. Influence of Bcl-2 Family Members on the Cellular Response of Small-Cell Lung Cancer Cell Lines to ABT-737. Cancer Research, vol. 67, 1176-83 (Copyright by American Association for Cancer Research, 2007).

Trudel, S. et al. The Bcl-2 Family Protein Inhibitor, ABT-737, Has Substantial Antimyeloma Activity and Shows Synergistic Effect with Dexamethasone and Melphalan. Clinical Cancer Research, vol. 13, 621-9 (Copyright by American Association for Cancer Research, 2007).

van Delft, M.F. et al. The BH3 mimetic ABT-737 targets selective Bcl-2 proteins and efficiently induces apoptosis via Bak/Bax if Mcl-1 is neutralized. Cancer Cell, vol. 10, 389-99 (Copyright by Elsevier Inc., 2006).

Galonek, H.L. & Hardwick, J.M. Upgrading the BCL-2 network. Nature Cell Biology, vol. 8, No. 12, 1317-9 (Copyright by Nature Publishing Group, 2006).

Zhang, H. et al. Bcl-2 family proteins are essential for platelet survival. Cell Death and Differentiation, vol. 14, 943-51 (Copyright by Nature Publishing Group, 2007).

Hotchkiss, et al., Cell Death, N. Engl. J. Med. (Oct. 15, 2009) 361:16, 1570-83.

Terrones, et al., BIM and IBID Are Not Mechanistically Equivalents When Assisting BAX to Permeabilize Bilayer Membranes, (Mar. 21, 2008) J. Biol. Chem. vol. 283 :7790-803.

Yin, et al., Bid-deficient mice are resistant to Fas-induced hepatocellular apoptosis, (Aug. 26, 1999) Nature vol. 400:886-91.

Bouillet et al., BH3-only Bcl-2 family member Bim is required for apoptosis of autoreactive thymocytes, (Feb. 2002) Nature 415:922-6.

Chen et al., Deficiency of Bim in dendritic cells contributes to overactivation of lymphocytes and autoimmunity, (2007) Blood 109:4360-7, Epub Jan. 16, 2007.

Carrington et al., BH3 mimetics antagonizing restricted prosurvival Bcl-2 proteins . . . (Jun. 15, 2010) Proc. Natl. Acad. Sci. U. S. A. 107: 10967-71.

Bardwell et al., The Bcl-2 Family Antagonist ABT-737 significantly inhibits multiple animal models of autoimmunity, (2009) J. Immunol. 182:7482-9.

Ghiotto et al., BH3-Only Proteins: The Death-Puppeteer's Wires, (2010) Cytometry A. 77:11-21.

Scatizzi, et al., Bim-Bcl-2 Homology 3 Mimetic Therapy . . . , (Feb. 2010), Arthritis Rheum. 62:441-51.

\* cited by examiner

TAT-BH3 METHODS FOR TREATING ARTHRITIS

CROSS-REFERENCE TO RELATED APPLICATIONS

This application is a non-provisional of and claims priority to U.S. Provisional Patent Application Ser. No. 60/901,591, filed Feb. 14, 2007, which document is hereby incorporated by reference herein to the extent permitted by law.

STATEMENT REGARDING FEDERALLY SPONSORED RESEARCH OR DEVELOPMENT

None.

REFERENCE TO A SEQUENCE LISTING, A TABLE, OR A COMPUTER PROGRAM LISTING COMPACT DISC APPENDIX

This application contains a Sequence Listing in paper and computer readable form which are hereby incorporated by reference in their entirety. The nucleic and amino acid sequences listed in the Sequence Listing are shown using standard letter abbreviations for nucleotide bases, and three letter code for amino acids. Only one strand of each nucleic acid sequence is shown, but the complementary strand is understood as included by any reference to the displayed strand.

BACKGROUND OF THE INVENTION

The present invention relates generally to compositions and methods for treating immune system mediated diseases such as rheumatoid arthritis (RA). RA is a destructive autoimmune disease that is a chronic inflammatory and destructive arthropathy of unknown etiology. RA is commonly associated with decreased life expectancy. RA causes the synovial lining to become hyperplastic leading to formation of pannus and destruction of cartilage and bone. In fact, RA may cause the synovial lining to increase from 1-2 cell layers to as much as 10 layers thick. The increase in synovial lining may be attributed to decreased death of both fibroblasts and macrophages since there is a paucity of apoptotic cells in RA, even though the milieu of the joint contains noxious factors that are normally detrimental to the survival of the cell. The induction of synoviocyte apoptosis in animal models of inflammatory arthritis, including streptococcal cell wall-induced arthritis, collagen-induced arthritis, HTLV-1 tax transgenic model, and RA explants in SCID mice result in either amelioration of the disease or reduction in joint inflammation and destruction. While the data from these animal studies suggest that increased apoptosis may be associated with an improved clinical outcome, the studies use adenoviral vectors, overexpression of FasL, or anti-Fas antibodies that are known to induce an inflammatory response. Thus, the applicability of these studies as a basis for therapies to treat RA is unclear and questionable.

Apoptosis in mammals proceeds through two distinct pathways, an "extrinsic" pathway that transduces an apoptotic signal following the ligation of death receptors on the cell surface and an "intrinsic" pathway in which mitochondria play a critical role. The induction of apoptosis mediated by the extrinsic pathway is initiated by binding of death ligands to their receptors. The intrinsic pathway is regulated by the Bcl-2 protein family which is divided into anti-apoptotic members (Bcl-2, Bcl-xL, Mcl-1, Al/Bfl-1 and Bcl-w) and pro-apoptotic members (Bax, Bak, Bad, Bim/Bod, Bok/Mtd, Bik/Blk/Nbk, Bid, Hrk/DP5, Bmf, Noxa, Puma/Bbc3). Bcl-2-related proteins contain Bcl-2-homology (BH 1-4) domains that are critical for homodimer and heterodimer formation between the family members. While the anti-apoptotic Bcl-2 like proteins contain at least three and possibly all four BH domains, the pro-apoptotic Bcl-2 related proteins are subdivided into two categories: (1) the multi-BH domain (BH1-3: e.g. Bak, Bax); and (2) the BH3-only proteins (e.g. Bad, Bim).

Many Bcl-2 family members are localized to the mitochondrial outer membrane and certain other intra-cellular membranes which suggest that mitochondrial dysfunction is involved in apoptosis. During intrinsic apoptosis signaling, the integrity of the outer mitochondrial membrane is lost, leading to the dissipation of the transmembrane potential through the opening of mitochondrial permeability transition pores and release of apoptogenic mitochondrial inter-membrane proteins, such as cytochrome c. In the cytoplasm, cytochrome c binds to the adaptor protein Apaf-1 which then causes aggregation and activation the initiator caspase 9. Caspase 9, in turn, activates the effector caspases 3 and 7 that cause the downstream degradative events in apoptosis. Apoptosis signaling through the intrinsic pathway is inhibited by overexpression of any of the Bcl-2 like pro-survival members or by loss of both multi-BH domain proteins Bak and Bax.

The BH3 domain is critical for cell death since deletion of the BH3 domain results in a failure to induce apoptosis in cells overexpressing the mutant constructs. The BH3 domain forms an amphipathic α-helix that binds to hydrophobic cleft on the surface formed by the BH1-3 domain of the anti-apoptotic Bcl-2 family members. Recent studies using peptides that correspond to the BH3 domains have shown that BH3-only proteins are also subdivided into two categories based on their ability to induce apoptosis. Bid and Bim are sufficient to sequester anti-apoptotic Bcl-2 family members, induce oligomerization of Bak and Bax, induce permeabilization of liposoines, and/or the release of cytochrome C. In contrast, Bad, Bmf, Hrk, Noxa, and Puma are sensitizers for apoptosis since they are only able to bind to the anti-apoptotic Bcl-2 members and require Bid or Bim to induce the death response.

Recent studies have examined the potential of altering the molecular rheostat that governs the Bcl-2 family through the use of BH3-domain peptides. However, to date, all studies that used BH3-peptidometrics have only examined their efficacy in xenograph tumor models and in immune-incompetent mice. Furthermore, since an increasing number of patients have failed to respond to traditional biologic therapy, which has a mode of action associated with increased apoptosis in the joint, it is clear that additional therapies are warranted.

The following references that are cited throughout this disclosure are hereby incorporated by reference in their entirety to the extent permitted by law. These references are used to illustrate certain aspects and backgrounds of the invention. However, the right to challenge the veracity of any statements made in these references is expressly reserved.

Pope, R. M. & Perlman, H. *Rheumatoid Arthritis. in Current Molecular Medicine: Principles of Molecular Rheumatology* (ed. Tsokos, G. C.) 325-361 (Humana Press Inc, Totowa, 2000).

Matsumoto, S., Muller-Ladner, U., Gay, R. E., Nishioka, K. & Gay, S. *Ultrastructural demonstration of apoptosis, Fas and Bcl-2 expression of rheumatoid synovial fibroblasts.* JRheum 23, 1345-1352 (1996).

Sugiyama, M. et al. *Localization of apoptosis and expression of apoptosis related proteins in the synovium of patients with rheumatoid arthritis.* Ann Rheum Dis 55, 442-449 (1995).

Liu, H. & Pope, R. M. *Apoptosis in rheumatoid arthritis: friend or foe.* Rheum Dis Clin North Am 30, 603-25, x (2004).

Adams, J. M. & Cory, S. *The Bcl-2 protein family: arbiters of cell survival.* Science 281, 1322-1326 (1998).

Kroemer, G. *The prolo-oncogene Bcl-2 and its role in regulating apoptosis.* Nature Meal 3, 614-620 (1997).

Opferman, J. T. & Korsmeyer, S. J. *Apoptosis in the development and maintenance of the immune system.* Nat Immunol 4, 410-5 (2003).

Green, D. R. & Reed, J. C. *Mitochondria and apoptosis.* Science 281, 1309-1312 (1998).

Zamnzami, N., Brenner, C., Marzo, I., Susin, S. A. & Kroemer, G. *Subcellular and submitochondrial mode of action of Bcl-2-like oncoproteins.* Oncogene 16, 2265-2282 (1998).

Yang, J. et al. *Prevention of apoptosis by Bcl-2: Release of cytochrome c from mitochondria blocked.* Science 275, 1129-1132 (1997).

Kluck, R. M., Bossy-Wetzel, E., Green, D. R. & Newmeyer, D. D. *The release of cytochrome c from mitochondria: A primary site for Bcl-2 regulation of apoptosis.* Science 275, 1132-1136 (1997).

Kuida, K. et al. *Reduced apoptosis and cytochrome c-mediated caspase activation in mice lacking caspase 9.* Cell 94, 325-337 (1998).

Rao, L. & White, E. *Bcl-2 and the ICE family of apoptotic regulators: making a connection.* Curr Opin Genet Dev 7, 52-58 (1997).

Perlman, H. et al. *Bcl-2 expression in synovial fibroblasts is essential for maintaining Mitochondrial homeostasis and cell viability.* Journal of Immunology 164, 5227-5235 (2000).

Harris, M. H. & Thompson, C. B. *The role of the Bcl-2 family in the regulation of outer mitochondrial membrane permeability.* Cell Death Differ 7, 1182-91. (2000).

Ahsen, O. V., Waterhouse, N. J., Kuwana, T., Newmeyer, D. D. & Green, D. R. *The 'harmless' release of cytochrome c.* Cell Death Differ 7, 1192-9. (2000).

Rathmell, J. C., Lindsten, T., Zong, W. X., Cinalli, R. M. & Thompson, C. B. *Deficiency in Bak and Bax perturbs thymic selection and lymphoid homeostasis.* Nat Immunol 3, 932-9 (2002).

Cheng, E. H. et al. *BCL-2, BCL-X(L) sequester BH3 domain-only molecules preventing BAX-and BAK-mediated mitochondrial apoptosis.* Mol Cell 8, 705-11 (2001).

Zong, W. X., Lindsten, T., Ross, A. J., MacGregor, G. R. & Thompson, C. B. *BH3-only proteins that bind pro-survival Bcl-2 family members fail to induce apoptosis in the absence of Bax and Bak.* Genes Dev 15, 1481-6 (2001).

Lindsten, T. et al. *The combined functions of proapoptotic Bcl-2 family members bak and bax are essential for normal development of multiple tissues.* Mol Cell 6, 1389-99 (2000).

Labi, V., Erlacher, M., Kiessling, S. & Villunger, A. *BH3-only proteins in cell death initiation, malignant disease and anticancer therapy.* Cell Death Differ (2006).

Letai, A. et al. *Distinct BH3 domains either sensitize or activate mitochondrial apoptosis, serving as prototype cancer therapeutics.* Cancer Cell 2, 183-92 (2002).

Certo, M. et al. *Mitochondria primed by death signals determine cellular addiction to antiapoptotic BCL-2 family members.* Cancer Cell 9, 351-65 (2006).

Chen, L. et al. *Differential targeting of prosurvival Bcl-2 proteins by their BH3-only ligands allows complementary apoptotic function.* Mol Cell 17, 393-403 (2005).

Willis, S. N. et al. *Proapoptotic Bak is sequestered by Mcl-1 and Bcl-xL, but not Bcl-2, until displaced by BH3-only proteins.* Genes Dev 19, 1294-305 (2005).

Kuwana, T. et al. *BH3 domains of BH3-only proteins differentially regulate Bax-mediated mitochondrial membrane permeabilization both directly and indirectly.* MolCell 17, 525-35 (2005).

Kim, H. et al. *Hierarchical regulation of mitochondrion-dependent apoptosis by BCL-2 subfamilies.* Nat Cell Biol 8, 1348-58 (2006).

Willis, S. N. et al. *Apoptosis initiated when BH3 ligands engage multiple Bcl-2 homologs, not Bax or Bak.* Science 315, 856-9 (2007).

Letai, A. *Pharmacological manipulation of Bcl-2 family members to control cell death.* J Clin Invest 115, 2648-55 (2005).

Goldsmith, K. C. et al. *BH3 peptidomimetics potently activate apoptosis and demonstrate single agent efficacy in neuroblastoma.* Oncogene 25, 4525-33 (2006).

Scatizzi, J. C., Bickel, E., Hutcheson, J., Haines, G. K., 3rd & Perlman, H. *Bim deficiency leads to exacerbation and prolongation of joint inflammation in experimental arthritis.* Arthritis Rheum 54, 3182-93 (2006).

Dai, S., Hirayama, T., Abbas, S. & Abu-Amer, Y. *The IkappaB kinase (IKK) inhibitor, NEMO-binding domain peptide, blocks osteoclastogenesis and bone erosion in inflammatory arthritis.* J Biol Chem 279, 37219-22 (2004).

Hirayama, T., Dai, S., Abbas, S., Yamanaka, Y. & Abu-Amer, Y. *Inhibition of inflammatory bone erosion by constitutively active STAT-6 through blockade of JNK and NF-kappaB activation.* Arthritis Rheum 52, 2719-29 (2005).

Kashiwagi, H. et al. *Tat-Bim Induces Apoptosis in Cancer Cells?* Annals of Surgical Oncology Submitted (2006).

Perlman, H. et al. *Differential expression pattern of the anti-apoptotic proteins, Bcl-2 and Flip in experimental arthritis.* Arthritis Rheum 44, 2899-908 (2001).

Pettit, A. R. et al. *TRANCE/RANKL knockout mice are protected from bone erosion in a serum transfer model of arthritis.* Am JPathol 159, 1689-99 (2001).

Liu, H. et al. *Mcl-1 is essential for the survival of synovial fibroblasts in rheumatoid arthritis.* J Immunol 175, 8337-45 (2005).

Busteed, S. et al. *Bcl-x(L) expression in vivo in rheumatoid synovium.* Clin Rheumatol (2006).

Brown, N. J. et al. *Fas death receptor signaling represses monocyte numbers and macrophage activation in vivo.* J Immunol 173, 7584-93 (2004).

Scatizzi, J. C. et al. *p21Cipl is required for the development of monocytes and their response to serum transfer-induced arthritis.* Am J Pathol 168, 1531-41 (2006).

Solomon, S., Rajasekaran, N., Jeisy-Walder, E., Snapper, S. B. & Illges, H. *A crucial role for macrophages in the pathology of K/BxN serum-induced arthritis.* Eur JImmunol 35, 3064-73 (2005).

Wipke, B. T. & Allen, P. M. *Essential role of neutrophils in the initiation and progression of a murine model of rheumatoid arthritis.* JImmunol 167, 1601-8 (2001).

Kyburz, D. & Corr, M. *The KRN mouse model of inflammatory arthritis.* Springer Semin Immunopathol25, 79-90 (2003).

Salmon, M. et al. *Inhibition of T cell apoptosis in the rheumatoid synovium.* J Clin Invest 99, 439-446 (1997).

Hilbers, I. et al. *Expression of the apoptosis accelerator Bax in rheumatoid arthritis synovium*. Rheumatol Int 23, 75-81 (2003).

Cha, H. S., Rosengren, S., Boyle, D. L. & Firestein, G. S. *PUMA regulation and proapoptotic effects in fibroblast-like synoviocytes*. Arthritis Rheum 54, 587-92 (2006).

Chen, M., Huang, L. & Wang, J. *Deficiency of Bim in dendritic cells contributes to over-activation of lymphocytes and autoimmunity*. Blood (2007).

Walensky, L. D. et al. *Activation of apoptosis in vivo by a hydrocarbon-stapled BH3 helix*. Science 305, 1466-70 (2004).

Lee, D. M. et al. *Mast cells: a cellular link between autoantibodies and inflammatory arthritis*. Science 297, 1689-92 (2002).

Dzhagalov, I., St John, A. & He, Y. W. *The antiapoptotic protein Mcl-1 is essential for the survival of neutrophils but not macrophages*. Blood 109, 1620-6 (2007).

Wipke, B. T., Wang, Z., Nagengast, W., Reichert, D. E. & Allen, P. M. *Staging the initiation of autoantibody-induced arthritis: a critical role for immune complexes*. J Immunol 172, 7694-702 (2004).

Letai, A. *Restoring cancer's death sentence*. Cancer Cell 10, 343-5 (2006).

Shore, G. C. & Viallet, J. *Modulating the bcl-2 family of apoptosis suppressors for potential therapeutic benefit in cancer*. Hematology Am Soc Hematol Educ Program, 226-30 (2005).

Letai, A. & Scorrano, L. *Laying the foundations of programmed cell death*. Cell Death Differ 13, 1245-7 (2006).

Chauhan, D. et al. *A novel Bcl-2/Bcl-X(L)/Bcl-w inhibitor ABT-737 as therapy in multiple myeloma*. Oncogene (2006).

Chen, S., Dai, Y., Harada, H., Dent, P. & Grant, S. *Mcl-1 down-regulation potentiates ABT-737 lethality by cooperatively inducing Bak activation and Bax translocation*. Cancer Res 67, 782-91 (2007).

Del Gaizo Moore, V. et al. *Chronic lymphocytic leukemia requires BCL2 to sequester prodeath BIM, explaining sensitivity to BCL2 antagonist ABT-737*. J Clin Invest 117, 112-21 (2007).

Konopleva, M. et al. *Mechanisms of apoptosis sensitivity and resistance to the BH3 mimetic ABT-737 in acute myeloid leukemia*. Cancer Cell 10, 375-88 (2006).

Oltersdorf, T. et al. *An inhibitor of Bcl-2 family proteins induces regression of solid tumours*. Nature 435, 677-81 (2005).

Tahir, S. K. et al. *Influence of Bcl-2 Family Members on the Cellular Response of Small-Cell Lung Cancer Cell Lines to ABT-737*. Cancer Res 67, 1176-83 (2007).

Trudel, S. et al. *The Bcl-2 Family Protein Inhibitor, ABT-737, Has Substantial Antimyeloma Activity and Shows Synergistic Effect with Dexamethasone and Melphalan*. Clin Cancer Res 13, 621-9 (2007).

van Delft, M. F. et al. *The BH3 mimetic ABT-737 targets selective Bcl-2 proteins and efficiently induces apoptosis via Bak/Bax if Mcl-1 is neutralized*. Cancer Cell 10, 389-99 (2006).

Galonek, H. L. & Hardwick, J. M. *Upgrading the BCL-2 network*. Nat Cell Biol 8, 1317-9 (2006).

Zhang, H. et al. *Bcl-2 family proteins are essential for platelet survival*. Cell Death Differ (2007).

BRIEF SUMMARY OF THE INVENTION

The present invention is directed to compositions and methods for treating immune system mediated diseases. In particular, certain embodiments of the present invention use BH3 mimetic therapy as an efficacious treatment of the effector phase of rheumatoid arthritis or other immune mediated disorders wherein the compositions and methods of the present invention markedly reduce the level of the Bcl-2 antagonist protein Bim present in RA synovial tissue as compared to control patients. Therefore, the present invention involves restoring the function of Bim in order to ameliorate inflammatory arthritis. In connection therewith, systemic delivery of a peptide to the BH3 domain of Bim effectively inhibits the development of K/BxN serum transfer-induced arthritis which closely resembles the effector phase of RA Moreover, the compositions and methods of the present invention exhibit a marked decreased in the edema of the ankle, in the histopathological arthritic scores, in the numbers of recruited neutrophils and macrophages, and in the production of pro-inflammatory factors in BH3 peptide-treated mice.

Moreover, since the anti-apoptotic proteins Bcl-2, Mcl-1, and Bcl-$x^L$ are highly expressed while expression of Bim is decreased in the RA joint and since mice deficient in Bim develop a more aggressive inflammatory arthritis, certain embodiments of the present invention utilize TAT-conjugated BH3 peptides to Bim in suppressing the development of experimental inflammatory arthritis. In one aspect, TAT-BH3 peptides are provided in a ten-fold less dosage form than has been previously used in cancer studies in order to prevent the development of inflammatory arthritis. The TAT-BH3 peptide-treatment of the present invention causes a reduced edema of the ankle; markedly lower histologic scores of arthritis, decreased production of IL-1β, MCP-1, and MMP-3, and fewer neutrophils and macrophages in the joint. The reduced development of arthritis corresponds with decreased numbers of neutrophils in peripheral blood and bone marrow.

Thus, in certain aspects, the present invention is directed to methods for treating immune-mediated disorders comprising administering a therapeutically effective amount of a composition including a cell delivery part and a cell death part. In another aspect, the invention is directed to a composition comprising a cell delivery part and a cell death part wherein the composition enters a cell to stimulate cell death. In certain embodiments, the immune mediated disorder is rheumatoid arthritis. In these or certain other embodiments, the cell delivery part is a cationic amphipathic peptide leader sequence and the cell death part is a proapoptotic peptide. In other aspects, the cell delivery part is a cationic amphipathic peptide leader sequence that is a Tat sequence, and the cell death part is a proapoptotic peptide that is a BH3 sequence.

Other aspects and advantages of the present invention will be apparent from the following detailed description of the preferred embodiment and the accompanying drawing figures.

BRIEF DESCRIPTION OF THE SEVERAL VIEWS OF THE DRAWING

In the accompanying drawings that form a part of the specification and that are to be read in conjunction therewith.

DETAILED DESCRIPTION OF THE INVENTION

Figure 1:
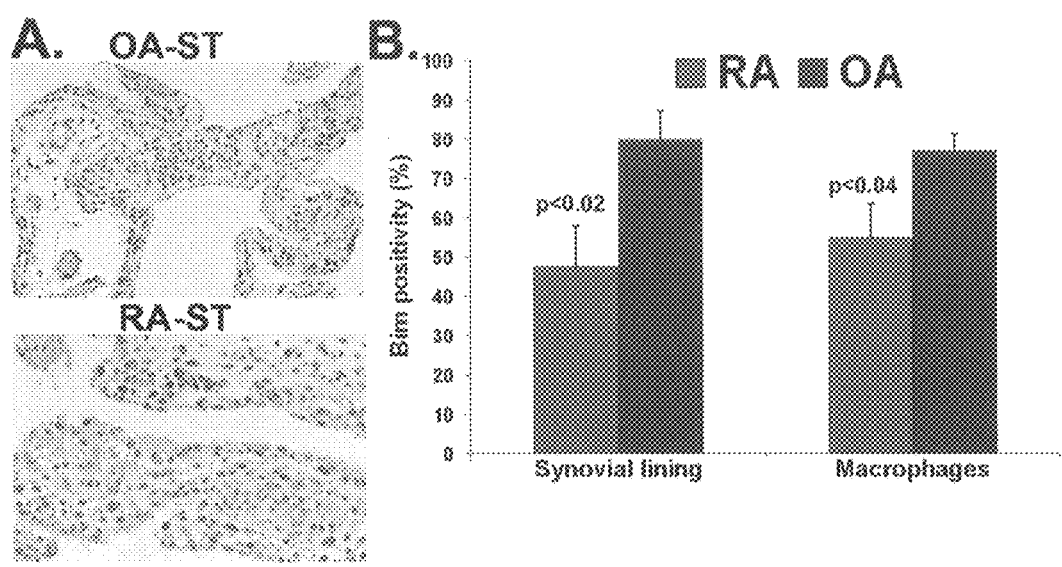
FIG. 1A is a representative photomicrograph of Bim expression in RA- and OA-STs showing a decrease of Bim expression in RA-ST as compared to OA-ST.
FIG. 1B is a representative bar chart showing Bim positivity in synovial lining and macrophages of the RA- and OA-STs of FIG. 1A.

The present invention provides a composition and method for treating a mammal suffering from an immune-mediated disorder or disease. Immune mediated disorders are pathogenic conditions which trigger a characteristic immune response by cells that include lymphocytes, antigen-presenting cells, and soluble mediators or cytokines produced by those cells. An immune-mediated disorder manifests itself in symptoms that include, but not are limited to, pain, inflammation, stiffness, and hearing loss. As used herein, immune-mediated disorders and/or diseases include, but are not limited to, rheumatoid arthritis, juvenile polyarticular rheumatoid arthritis, Still's disease, Sjogrens Syndrome, vasculitis, Systemic Lupus Erythmatosus, peripheral neuropathy, Raynauds Phenomenon, sensory-neural hearing loss (Meniere's Disease), fibromylagia, inflammatory bowel disease (ulcerative colitis, Crohn's disease, and mucinous colitis), psoriatic arthritis, Reiter's Syndrome, ankylosing spondylitis, temporal arteritis, polymyalgia rheumatica and agammaglobulinemia. Immune-mediated disorders also include autoimmune diseases including, but not limited to, acute disseminated encephalomyelitis, Addison's disease, ankylosing spondylitis, antiphopholipid antibody syndrome, aplastic anemia, autoimmune hepatitis, autoimmune oophoritis, celiac disease, Crohn's disease, diabetes mellitus type 1, gestational pemphigolid, Goodpasture's syndrome, Graves' disease, Guillain-Barré syndrome, Hashimoto's disease, idiopathic thrombocytopenic purpura, Kawasaki's disease, lupus erythematosus, mixed connective tissue disease, multiple schlerosis, myasthenia gravis, opsoclonus myoclonus syndrome, optic neuritis, Ord's thyroiditis, pemphigus, pernicious anaemia, polyarthritis, primarily biliary cirrhosis, rheumatoid arthritis, Reiter's syndrome, Sjögren's syndrome, Takayasu's arteritis, temporal arteritis, warm autoimmune hermolytic anemia, and Wegener's granulomatosis. Further, diseases suspected or theorized to be linked to autoimmunity include alopecia universalis, Behcet's disease, Chagas' disease, chronic fatigue syndrome, dyasautonomia, endometriosis, hidradenitis suppurativa, interstitial cystitis, Lyme disease, morphea, neuromyotonia, narcolepsy, psoriasis, sarcoidoisis, schizophrenia, schleroderma, ulcerative colitis, unveitis, vitiligo, and vulvodynia.

In rheumatoid arthritis and other immune-mediated diseases, there may be a shift in the balance towards increased expression of the anti-apoptotic Bcl-2 members. There are an increased number of cells positive for Bcl-2 in RA synovium as compared to osteoarthritis (OA) synovial tissue. Further, there are more Mcl-1 expressing cells in the RA joint as compared to controls. It has been demonstrated that Bcl-$x_L$ expression is increased in RA synovial tissue as compared to controls. While lining thickness does not correlate with Mcl-1 expression, lining thickness and inflammatory score correlates with the frequency of Bcl-2-positive cells thereby suggesting that increased Bcl-2 expression in the synovial lining may be associated with worse outcome in RA. Consistent with Bcl-2 being highly expressed in the RA joint, higher levels of Bcl-2 mRNA in RA as compared to OA synovial tissue are observed by in-situ hybridization. Interestingly, the expression of inactivated Bax is shown to be elevated in RA synovial tissue as compared to healthy controls.

The expression of Puma has been shown to be localized to the sublining and not to the synovial lining region. Since there are few apoptotic cells in the joint, it is believed that the increased expression of Bax and Puma is insufficient to induce apoptosis in the RA joint. However, expression of Bim is reduced in RA as compared to control synovial tissue. Thus, the present invention is based on the concept that the molecular rheostat that governs the survival of cells is shifted toward the Bcl-2 pro-survival proteins. Moreover, it is known that RA synovial fibroblasts treated with RNAi to Bim fail to undergo apoptosis induced by anti-sense to Mcl-1, and the percent reduction in death observed in Bim-RNAi treated RA synovial fibroblasts is equivalent to RNAi-Bak/Bax treated fibroblasts. Expression of Bim is therefore believed to be as essential for death as is the expression of Bak and Bax in RA synovial fibroblasts.

Furthermore, the role that multi-BH domain and BH3 proteins play in the development of a mouse model of arthritis has been investigated. Mice deficient in Bak or Bax develop inflammatory arthritis similar to control mice. In contrast, mice lacking Bim develop more aggressive and worse forms of inflammatory arthritis even compared to Bid−/− mice (data not shown). Further, deficiency in Bim also results in enhanced activation of dendritic cells and macrophages (data not shown). In this aspect of the present invention, it is shown that a decrease in expression of Bim may lead to enhance progression of inflammatory arthritis and that systemic delivery of the BH3 domain to Bim is dramatically effective at suppressing the development of K/B×N serum transfer-induced arthritis, which closely resembles the effector phase of RA. In accordance with the present invention, treatment with TAT-BH3 peptides also results in markedly less edema of the ankle, decreased histological scores of arthritis, reduced recruitment of neutrophils and macrophages, and less production of pro-inflammatory factors in the joints. Of note, the dose of the TAT-BH3 peptides used in the present invention is almost five-fold less than the dose used in known cancer studies and fewer injections are required. The reduced dose of TAT-BH3 peptides may explain the limited toxicity observed in arthritic mice. Thus, TAT-conjugated peptides to the BH3 domain have significant potential as a therapy for RA.

While not wished to be bound by theory, the KfB×N serum transfer model of arthritis requires mast cells, inflammatory monocytes, macrophages, and neutrophils. Mice treated with BH3 peptides have very few macrophages or neutrophils recruited to the joints as compared to control mice. However, only the numbers of circulating and bone marrow neutrophils appear to be impaired in TAT-BH3 treated mice. This for the reason that neutrophils are susceptible to BH3 peptides. Mcl-1 has been shown to be required for development of neutrophils but not monocytes or macrophages whereas, in the present invention, the BH3 peptide to Bim is shown to have a high affinity for Mcl-1, which is unlike other BH3 mimetics including ABT-737. Previous investigations have suggested a staging model for the development of K/B×N serum transfer-induced arthritis. However, since neutrophils are required for one of the early steps in K/B×N serum transfer induced arthritis model, it is believed that suppression of neutrophils leads to reduced recruitment of macrophages and less production of pro-inflammatory factors. While the K/B×N model of arthritis closely resembles the effector phase of RA and each model of inflammatory arthritis shares common phenotypic characteristics of RA, previous studies using BH3 mimetic therapy have focused on the feasibility in treating cancer whereas the present invention is directed to the efficacy of treating an immune-mediated disorder with BH3 mimetics. Recent studies have employed the BH3 mimetic, ABT-737 which is a small based molecule, as a single agent for certain cancers including lymphoma, myeloma, leukemia, and small lung carcinoma. However, mechanistically ABT-737 behaves similarly to the sensitizer class of BH3-only proteins. Further, ABT-737 has no effect on cells that express high levels of Mcl-1. In contrast, BH3 peptides to Bim are shown to be effective at suppressing the anti-apoptotic effects of all the pro-survival Bcl-2 members including Mcl-1. Further, BH3 peptides have a minimal effect on platelet counts, while ABT-737 is shown to have dramatic effect on platelet numbers. Thus, it is believed that BH3 peptide to Bim may have a greater therapeutic value in disorders such as RA or other autoimmune diseases where a failure to delete the autoreactive cells leads to its pathogenesis.

BH3 Mimetic Therapy

BH3 mimetic therapies can be formulated in a pharmaceutical composition for administration to a mammalian patient. As used herein, a "pharmaceutical composition" includes the active agent and a pharmaceutically acceptable carrier, excipient or diluent. The phrase "pharmaceutically acceptable" refers to molecular entities and compositions that are physiologically tolerable and do not typically produce a severe allergic or similar untoward reaction when administered to a mammal. Preferably, as used herein, the term "pharmaceutically acceptable" means approved by a regulatory agency of the Federal or a state government or listed in the U.S. Pharmacopoeia or other generally recognized pharmacopoeia for use in animals, and more particular in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or other aqueous solutions, saline solutions, aqueous dextrose and glycerol solutions are preferably employed as carriers, particularly for injectable solutions. Suitable pharmaceutical carriers are described in "Remington's Pharmaceutical Sciences" by E. W. Martin.

For human therapy, the pharmaceutical compositions, including the active agents, will be prepared in accordance with good manufacturing process (GIMP) standards as set by the Food & Drug Administration (FDA). Quality assurance (QA) and quality control (QC) standards will include testing for purity and function, homogeneity and function, and/or other standard measures.

In order to treat an immune-mediated disorder and/or its symptoms, the pharmaceutical composition hereof is administered by any route that will permit delivery of the active agent to the affected cells. Since it is believed that BH3 mimetic therapy does not harm normal cells, systemic administration of the active agent is acceptable. Preferably, administration is intraperitoneal and also including, but not limited to, intra-arteriole, intramuscular, intradermal, subcutaneous, perenteral, intraventricular, and intracranial administration. Alternatively, the active agent may be delivered locally to the affected cells by any suitable means.

In therapeutic treatments of the invention, a therapeutically effective amount of the pharmaceutical composition is administered to a mammalian patient. As used herein, the term "therapeutically effective amount" means an amount sufficient to reduce by at least about 15 percent, preferably by at least 50 percent, more preferably by at least 90 percent, and most preferably prevent, a clinically significant deficit in the activity, function and response of the patient. Specifically, a therapeutically effective amount will cause one or more of the following: decreased edema; decreased histopathological arthritic scores, decreased numbers of recruited neutrophils and macrophages, and decreased production of pro-inflammatory factors. The frequency and dosage of the therapy can be titrated by the ordinary physician or veterinarian using standard dose-to-response techniques that are well known in the art.

As noted above, certain embodiments of the present invention involve the use BH3 mimetic therapy as an efficacious treatment of the effector phase of rheumatoid arthritis or other immune mediated disorders. In particular, a pharmaceutically effective amount of a pharmaceutical composition for treatment of an immune-mediated disorder hereof is administered to a mammalian patient. Preferably, of from about 0.1-10 mg/kg per day, and more preferably of from about 1-8 mg/kg per day, and most preferably of from about 2-6 mg/kg per day of the pharmaceutical composition is administered to a patient.

The pharmaceutical composition includes an active agent composed of at least one cell delivery agent and at least one cell death agent. In certain embodiments, the cell delivery agent is a cell-penetrating peptide (CPP). A CPP is a peptide vector that can traverse through the plasma membrane barrier without breaching the integrity of the cell, and deliver a desired cargo inside the cell. The range of cargoes that can be delivered intracellularly by CPPs encompasses a broad variety of hydrophilic molecules, such as peptides, proteins, antibodies, imaging agents, DNA and even nanosized entities, including polymer-based systems, solid nanoparticles and liposomes. In certain embodiments, the CPP hereof is preferably a cationic amphipathic peptide leader sequence and, more preferably, a TAT sequence. In certain other embodiments, the CPP is selected from the group consisting of TAT, penetratin, VP22, transportan, synthetic oligoarginines, and combinations thereof. One skilled in the art will appreciate, however, that any vector capable of traversing the plasma membrane barrier without breaching the integrity of the cell and capable of delivering a desired active agent inside the cell may be used in the present invention without departing from the scope thereof.

The pharmaceutical composition for treatment of an immune-mediated disorder hereof also includes a cell death agent capable of stimulating cell death. In certain embodiments, the cell death agent is preferably a composed of at least one proapoptotic peptide selected from the group consisting of Bax, Bak, Bad, Bim/Bod, Bok/Mtd, Bik/Blk/Nbk, Bid, Hrk/DP5, Bmf, Noxa, Puma/Bbc3, and combinations thereof. In certain other embodiments, the cell death agent is a BH3 (Bcl-2 homology domain 3 only) protein sequence selected from the group consisting of Noxa, Bim, Puma, Bmf, Bad, Bik, Hrk, Bid and combinations thereof.

In certain embodiments of the present invention, the pharmaceutical composition described herein can be used to restore the function of the Bcl-2 antagonist protein Bim in order to ameliorate certain symptoms of an immune-mediated disorder. In particular, the systemic delivery of the pharmaceutical composition hereof to the BH3 domain of Bim is used to inhibit the effector phase of RA.

EXAMPLE

The seven-week-old progeny from homozygous KRN TCR transgenic mice (C57BL/6 background) crossed with non-obese diabetes (NOD) mice (K/BxN) were euthanized, peripheral blood was isolated, and serum were collected and pooled. One hundred and fifty microliters of K/BxN serum were intraperitoneally injected on each flank of 6-week old wt mice. At the time of injection of serum and at days 2 and 4 post-serum injection, 2 mg/kg of TAT-BH3 peptides and TAT-inactive BH3 peptides intraperitoneally injected into the mice. This dose has been shown to be appropriate to suppress NF-κB and STAT6 using TAT-conjugated peptides and proteins in mouse models of arthritis.

The peptides from BH3 domain of Bim were constructed as follows:

(SEQ ID NO: 1) TAT-BH3:
Ac-RKKRR-Orn-RRR-EIWIAQELRRIGDEFNAYYAR-OH;

(SEQ ID NO: 2) TAT-BIM inactive (TAT-inactive BH3):
Ac-RKKRR-Orn-RRR-EIWIAQEARRIGAEFNAYYAR-OH The TAT-inactive BH3 peptides have two point mutations L152A and D157A that prevent association with Bcl-2 anti-apoptotic proteins and do not activate Bak or Bax. At each time point and prior to euthanasia, the degree of arthritis as indicated by joint swelling was quantitated by measuring two perpendicular diameters of the ankles using a caliper (Lange Caliper: Cambridge Scientific Industries, Cambridge Mass.). Joint circumference was calculated using the geometric formula of ellipse circumference $(2\pi X \sqrt{(a^2+b^2)/2})$. Following euthanasia, serum was isolated from peripheral blood by cardiac stick and ankle joints were removed. One of the ankle joints was fixed in 10% neutral buffered formalin for 24 hours, decalcified in EDTA-decalcification buffer for two weeks, embedded in paraffin, and sectioned. The other ankle joint was placed in liquid nitrogen, grounded into a fine powder by mortal and pestle, digested in protein lysis buffer (150 μm NaCl, 0.5% NP-40, 50 mM Tris, and 2 mM EDTA) in the presence of phosphatase and protease inhibitors, and homogenized on ice for 20 seconds. To examine any toxicity due to systemic delivery of TAT-Bim peptides, alkaline phosphatase (ALP), alanine transaminase (AST), alanine aminotransferase (ALT), and blood urea nitrogen levels were measured.

Paraffin embedded ankle or liver sections were stained with hematoxylin and eosin (H&E), Safranin O and methyl green. Histopathological scoring was performed and ankle sections were evaluated by examining at least 3 sections/ankle and 3 fields/section at 400× magnification. H&E ankle sections were scored on a 0-5 scale for inflammation, with 0=normal, 1=minimal infiltration, 2=mild infiltration, 3=moderate infiltration, marked infiltration, mad 5=severe infiltration. Bone erosion was scored on a 0-5 scale by viewing H&E ankle sections, with 0=no or normal bone resorption, 1=small areas of resorption, 2=more numerous areas of resorption, 3=obvious resorption, 4=full thickness defects in the bone without distortion of the profile, 5=full thickness defects in the bone with distortion of the profile. H&E ankle stained sections were scored on a 0-5 scale for pannus formation, with 0=no pannus formation, 1=minimal pannus formation, 2=mild pannus formation, 3=moderate pannus formation, 4=marked pannus formation, and 5=severe pannus formation. H&E and Safranin 0 and methyl green sections were scored on a 0-5 scale for cartilage damage, with 0=no damage, 1-2=superficial cartilage destruction, 3-4=cartilage destruction to middle zone, 5=cartilage destruction to tide mark. Polymorphonuclear (PMN) leukocyte infiltration: 0=no PMNs, 1=rare scattered PMNs, 2=more frequent scattered PMNs, 3=small clusters of PMNs, 4=larger clusters of PMNs, mad 5=sheets of PMNs (abscess). Histopathological scoring was conducted on an Olympus BX40 microscope (1000×). Photographs were taken on a Nikon microscope equipped with the Nikon digital camera DMX 1200.

For detection of mouse IL-1β, TNFα, MCP-1, KC, or MMP-3 in ankle extracts, sandwich ELISAs were performed according to the manufacturer's instructions (R & D Systems, Minneapolis, Minn.). The sensitivity for all cytokines was 15.6 pg/mL for IL-1β and KC, 7.813 pg/mL for TNFα and MCP-1, and 0.312 ng/mL for MMP3. ELISAs were quantitated by absorbance at 450 nm on a microplate reader (Bio-Rad, Hercules, Calif.). Data obtained using ELISA on ankle extracts were normalized by the total protein concentration (μg/μL) for each individual ankle extract.

Peripheral blood and bone marrow were isolated from mice following euthanasia. Total leukocyte numbers were determined using an automated hematology analyzer ABX Pentra 60 (Diamond Diagnostics, Inc, Holliston, Mass.). The red blood cells in peripheral blood were lysed and the remaining cells were fixed with BD FACS lysing solution (BD Biosciences, Pharmingen) following incubation with antibodies. Bone marrow cells were isolated by flushing Dulbecco's Modified Eagle Medium (DMEM) (Gibco, Grand Island, N.Y.) through the tibias and red blood cells were lysed with BD PharM Lyse (BD Biosciences, Pharmingen) prior to incubation with antibodies. Cells with incubated with Fc Block (BD Biosciences, Pharmingen) then stained with fluorochrome conjugated antibodies to CD45, CD11b, Gr-1, CD62L, Ly-6C, Ly-6G, CD31 (BD Biosciences, Pharmingen) or isotype control antibodies for 30 minutes. Cells were acquired on a BD LSRII (BD Biosciences, Pharmingen) using Diva Software at the Saint Louis University Core Flow Cytometry Facility. All analysis was performed using FlowJo software (Tree Star Inc.).

Results were expressed as the mean±standard error. Differences between groups were analyzed using Student's t test. Decreased expression of Bim in RA as compared to osteoarthritis (OA) synovial tissue (ST) was observed. Previous investigations have demonstrated a lack of apoptotic cells in RA–STs and increased expression of anti-apoptotic Bcl-2 family members. To date, the expression of the pro-apoptotic protein Bim in RA synovial tissue has not been examined. Therefore, the expression of Bim was characterized to define a potential mechanism responsible for resistance to apoptosis in these tissues. There was an increase in average synovial lining thickness (2.4±0.2 vs. 1.7±0.4; p<0.06) and inflammation score (3.4±0.5 vs. 1.6±0.3; p<0.01) in RA–(n=8) as compared to OA–(n=8) STs. Immunohistochemical analysis revealed decreased expression of Bim in RA– as compared to OA–STs as shown in FIGS. 1A and 1B. The staining pattern for Bim was a granular cytoplasmic staining consistent with cytoplasmic and mitochondrial staining. Fewer numbers of RA–synovial lining (48±10.4% vs. 80±7.2%; p<0.02) cells were positive for Bim as compared to OA–STs as seen in FIG.

1B. Staining with normal control IgG was negative for both RA (not shown) and OA–ST (data not shown). Further examination of adjacent sections stained for CD68 (macrophages) and Bim revealed a decrease in Bim expression in the macrophage population in RA synovial tissue as compared to OA synovial tissue as shown in FIG. 1B. There was no difference in expression of Bim in lymphocytes, fibroblasts, endothelial cells, or blood vessels in RA and OA ST (data not shown).

Figure 2:
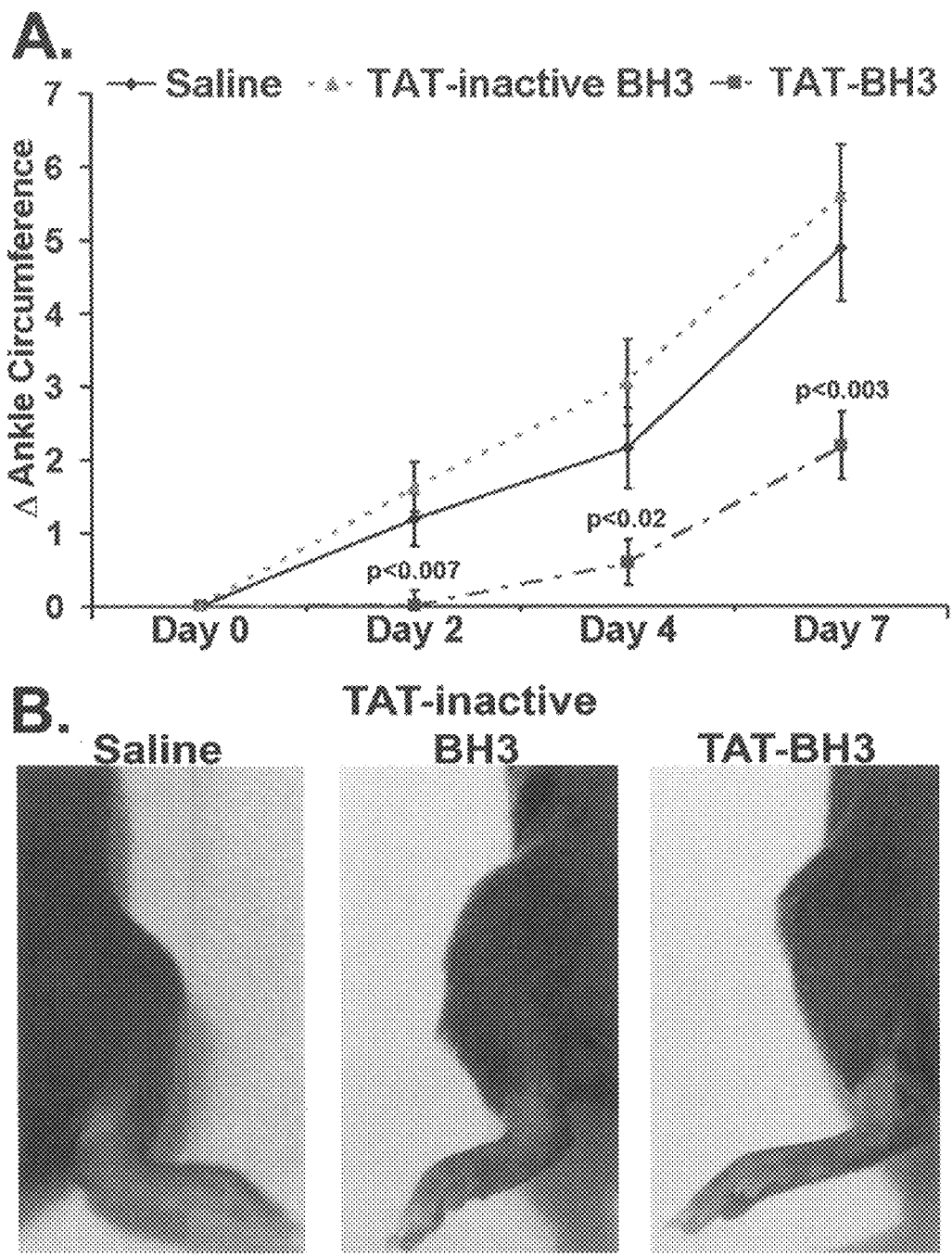
FIG. 2A is a representative graph of the ankle circumference of mice treated with TAT-BH3 peptides.
FIG. 2B is a representative series of photographs showing the ankle joints from saline-, TAT-inactive BH3-, and TAT-BH3-peptide treated mice of FIG. 2A.

Peptides to the BH3 domain of Bim were observed to suppress edema formation in arthritic ankles. Since the expression of Bim is decreased in RA as compared to OA synovial tissue and since the lack of Bim is essential for enhancing the arthritic response in mice, these data demonstrate that Bim is potential biological target for inflammatory arthritis. Therefore, peptides to the BH3 domain of Bim were used that are fused to polycationic peptide derived from HIV-1 TAT. These peptides have shown to activate Bak and Bax, suppress Bcl-2 and Mcl-1, induce mitochondrial permeability, and release mitochondrial cytochrome c. Mice were intraperitoneally injected with K/BxN serum to induce the effector phase of inflammatory arthritis. At one hour after injection of serum, mice were subjected to a second intraperitoneal injection of TAT-inactive BH3 or TAT-BH3 peptides (2 mg/kg). Mice were intraperitoneally injected with additional doses of TAT-inactive BH3 or TAT-BH3 peptides at days 2 and 4. There was appreciable development of inflammatory arthritis as early as day 2 following injection with K/BxN serum in saline and TAT-inactive BH3 peptide-treated mice. Saline and TAT-inactive BH3 peptide treated mice had 1.2 mm ($p<0.007$) and 1.6 mm ($p<0.001$) change in ankle circumference at day 2, while TAT-BH3 peptide-treated mice had only a 0.1 mm change in ankle circumference (FIG. 2A). Treatment with TAT-BH3 peptides dramatically reduced the development of arthritis by 80% ($p<0.02$) and 72% ($p<0.001$) as compared to saline and TAT-inactive BH3 peptide treated mice, respectively at day 4. Further, there was a 55% ($p<0.003$) and 61% ($p<0.001$) inhibition of arthritis in TAT-BH3 peptide treated as compared to saline and TAT-inactive BH3 peptide treated mice by day 7 post-K/BxN serum injection as shown in FIGS. 2A and 2B. There was no statistical difference between saline and TAT-inactive BH3 peptide-treated mice.

Figure 3:
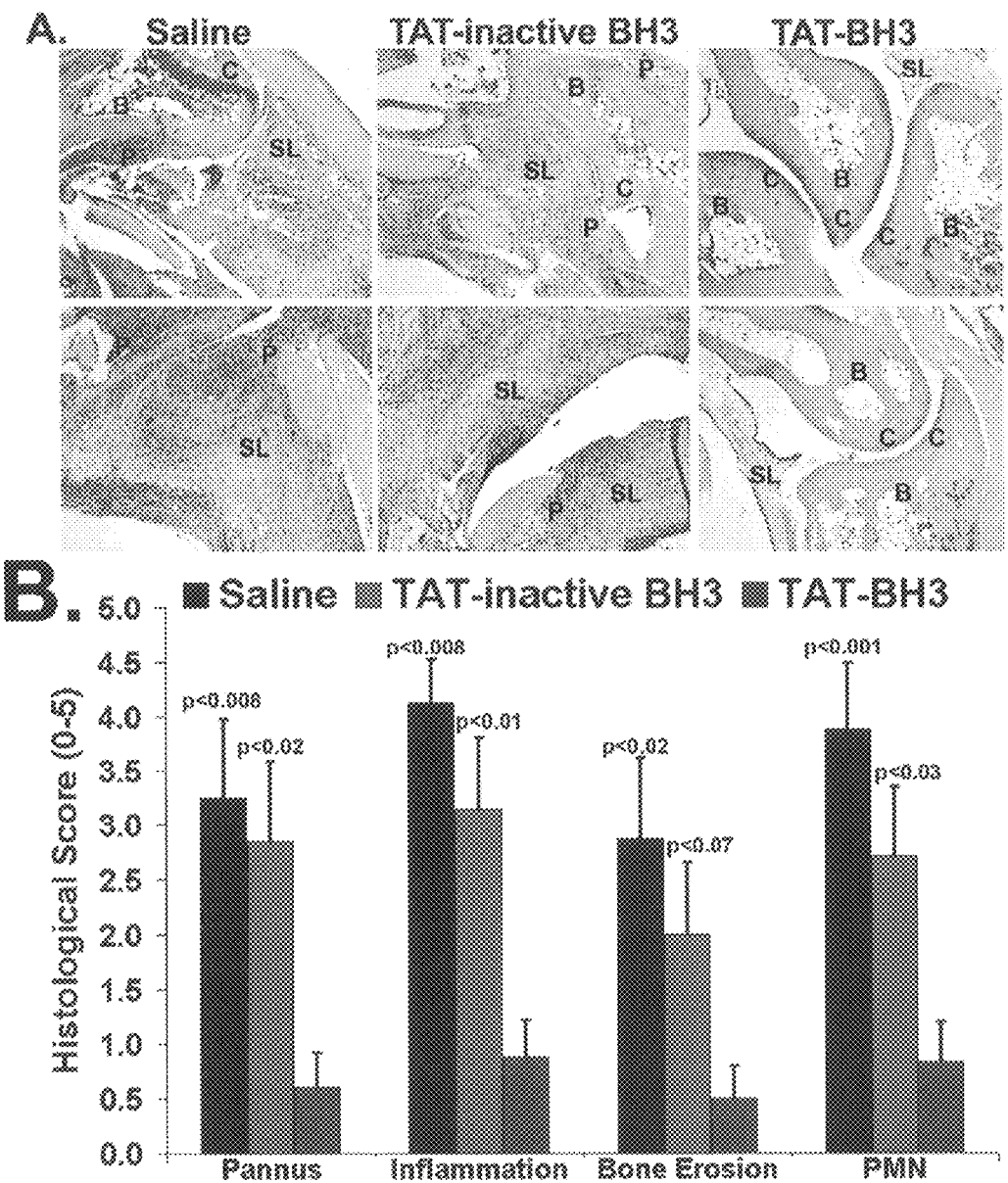
FIG. 3A is a representative photomicrograph of safranin O- and methyl green-stained ankle sections of TAT-BH3 peptide treated mice.
FIG. 3B is a representative bar chart showing macrophage recruitment in the ankle sections of FIG. 3A.

TAT-BH3 peptide-treated mice were observed to have reduced arthritic scores. To accurately assess the degree of inflammation and destruction of cartilage and bone, ankle sections were examined using a histopathological scoring system on hematoxylin and eosin (H& E) or safranin O-methyl green stained ankle sections. TAT-BH3 peptide-treated mice had little pannus formation, cellular inflammation, or bone erosion as compared to TAT-inactive BH3 peptide- or saline-treated mice as seen in FIGS. 3A and 3B. TAT-BH3 peptides suppressed pannus formation by 79% as compared saline or TAT-inactive BH3 peptide treated mice as shown in FIG. 3B. The lack of pannus formation in TAT-BH3 peptide-treated mice was associated with 71% decrease in bone erosion score as compared to saline- or TAT-inactive BH3 peptide treated mice. Further, there was a 72% reduction in inflammation in TAT-BH3 peptide-treated as compared to saline- or TAT-inactive BH3 peptide-treated mice. There was no statistical difference in histological scores in saline- or TAT-inactive BH3 peptide-treated mice thereby demonstrating that treatment with TAT-BH3 peptides lead to decreased physical and cellular inflammation.

Figure 4:
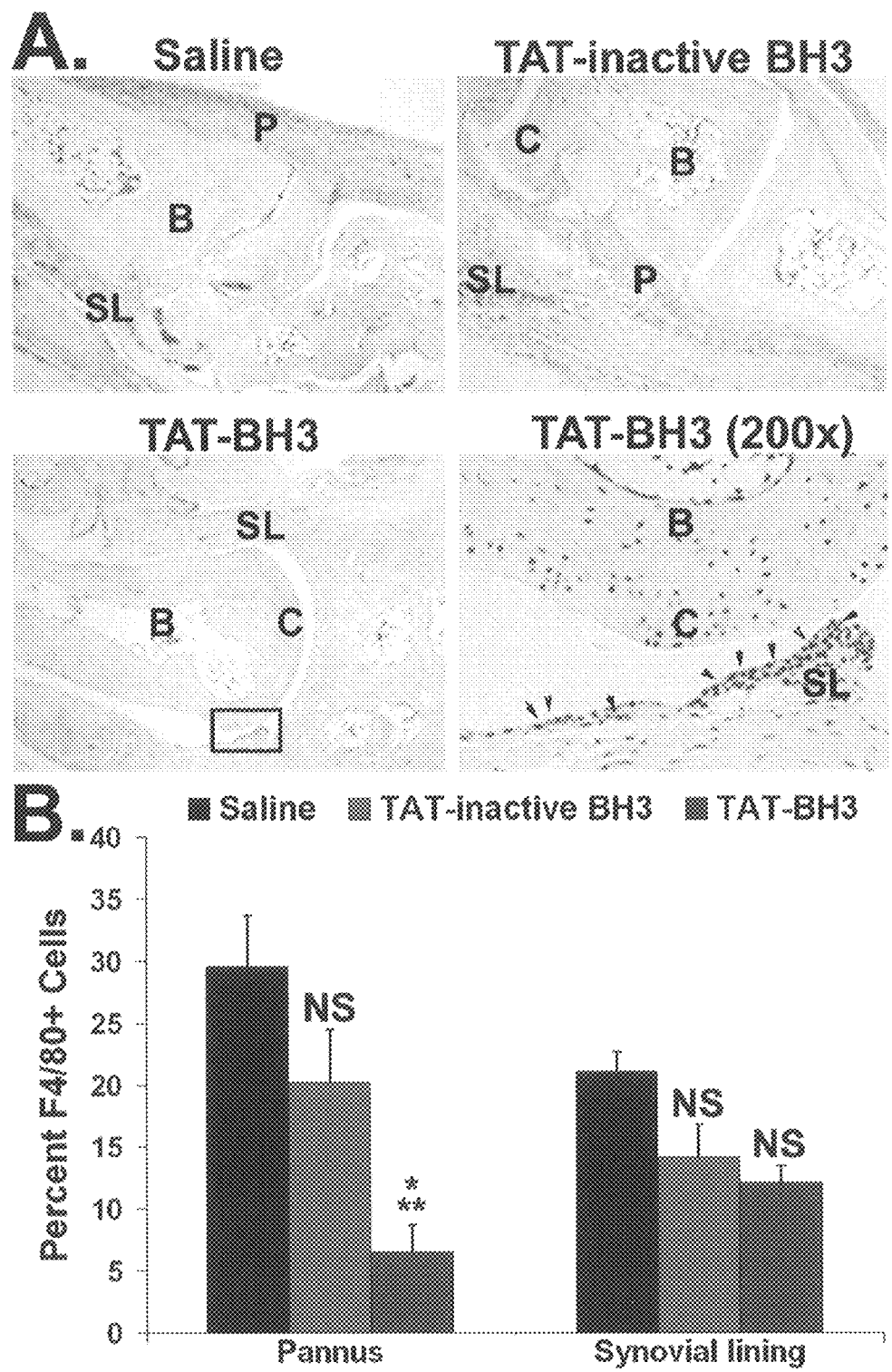
FIG. 4A is representative photomicrograph of ankle sections stained for F4/80 antigen from saline- and BH3-peptide treated mice.
FIG. 4B is a representative bar chart showing macrophage recruitment in the ankle sections of FIG. 4A.

TAT-BH3 peptides treatment reduces the numbers of myeloid cells in arthritic joints. Neutrophils and macrophages are required for the development of K/BxN serum transfer induced arthritis 40-42. To this end, the numbers of polymorphonuclear cell and macrophages in saline and BH3 peptide arthritic mice were quantified. TAT-BH3 peptide-treated mice showed a 69% reduction in PMN score as compared to TAT-inactive BH3 peptide- or saline-treated mice (FIG. 3B). There was a 77% ($p<0.001$) and 68% ($p<0.02$) decrease in the numbers of macrophages within the pannus region in TAT-BH3 peptide-treated mice as compared to saline- or TAT-inactive BH3 peptide-treated mice, respectively (FIGS. 4A, B). There was no statistical difference in average number of macrophages in the synovial lining in TAT-BH3 peptide as compared to TAT-inactive BH3 peptide-treated mice (FIG. 4B) thereby demonstrating that the suppression of arthritis by TAT-BH3-peptide treatment is associated with reduced numbers of neutrophils and macrophages. Treatment with TAT-BH3 peptides were observed to lead to decreased production of pro-inflammatory factors in arthritic joints. The milieu of the RA joint is crucial for the initiation and the perpetuation of inflammatory arthritis. Previous studies have shown that mice lacking Bim display increased levels of pro-inflammatory factors in the joint that is associated with increased numbers of neutrophils and macrophages and more articular destruction. However, the present invention indicates that the loss of Bim greatly affects the environment of the arthritic joint so the levels of IL-1β, TNFα, MCP-1, KC, and MMP-3 in the joints of saline- and BH3 peptide-treated mice. The level of IL-1β was decreased by 37% ($p<0.08$), while there was no change in the level of TNFα in TAT-BH3 peptide treated as compared to saline- or TAT-inactive BH3 peptide-treated mice as shown in Table 1 hereinbelow. The production of KC and MCP-1 was diminished by 28% (NS) and 47% ($p<0.06$) respectively, in TAT-BH3 peptide-treated as compared to saline- or TAT-inactive BH3 peptide-treated mice. Further, levels of MMP-3 were reduced by 47% ($p<0.07$) in TAT-BH3 peptide treated as compared to saline- or TAT-inactive BH3 peptide-treated mice. There were no differences in circulating levels of IL-1β, TNFα, MCP-1, and KC in serum of saline, TAT-inactive BH3 peptide-, or TAT-BH3 peptide-treated mice (data not shown) thereby demonstrating that treatment with TAT-BH3 peptides is crucial in limiting the local inflammatory milieu, particularly factors that are known to be required for development of K/BxN serum transfer induced arthritis.

TABLE 1

Pro-inflammatory molecule production in ankle joints following transfer of K/BxN serum.

| | IL-1β | TNFα | MCP-1 | KC | MMP-3 |
| --- | --- | --- | --- | --- | --- |
| TAT-BH3 (n = 14) | 522 ± 127 | 4.5 ± 0.3 | 131 ± 28 | 308 ± 78 | 9 ± 3 |
| TAT-inactive BH3 (n = 8) | 824 ± 103 ($p < 0.08$) | 4.4 ± 0.3 | 196 ± 17 ($p < 0.06$) | 428 ± 45 | 17 ± 4 ($p < 0.07$) |

Mice were euthanized at seven days post-serum transfer. Ankle joints from each mouse were isolated, snap frozen, grounded into a fine powder, lysed, and examined for IL-1β, TNFα, MCP-1, KC, and MMP-3 production using an ELISA. Data are shown as μg/μL per joint. Values represent the mean±standard error, which were compared by Student's t-test.

Figure 6:
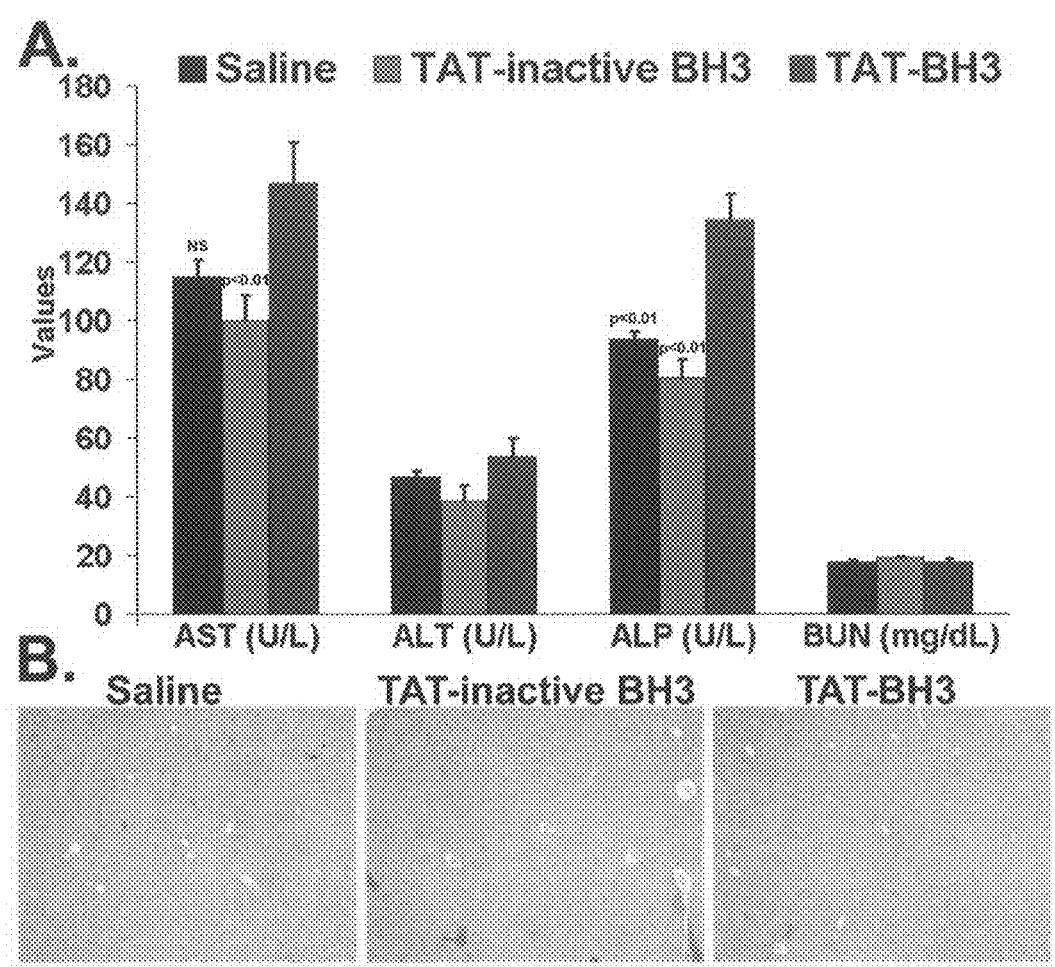
FIG. 6A is a representative bar chart showing limited toxicity in TAT-BH3 peptide treated mice wherein liver enzymes are marginally effected by TAT-BH3 peptide.
FIG. 6B is a representative photomicrograph of liver sections of the mice of FIG. 6A.

TAT-BH3 peptides were observed to have limited toxicity in arthritic mice. Since previous reports have suggested that at higher concentrations TAT-BH3 peptides may have toxic effects, the levels of alkaline phosphatase, alanine transaminase (AST), alanine aminotransferase (ALT), and blood urea nitrogen in saline-, TAT-inactive BH3 peptide, and TAT-BH3-treated arthritic mice were examined. There was statistical difference in ALT and BUN levels in TAT-BH3, TAT-inactive BH3 and saline treated arthritic mice. There was a 1.3-fold ($p<0.1$) and 1.5-fold ($p<0.01$) increase in AST levels and a 1.4-fold ($p<0.01$) and 1.7-fold ($p<0.01$) increase in ALP levels in TAT-BH3 peptide as compared to saline- and TAT-inactive BH3-treated arthritic mice as shown in FIG. 6A. However, there were no gross histologic abnormalities in the livers of saline-, TAT-inactive BH3 peptide, and TAT-BH3-treated arthritic mice as shown in FIG. 6B. TAT-BH3 peptides did not reduce the number of circulating leukocytes, splenocytes, (data not shown) or red blood cells (Table 2) as compared to TAT-inactive BH3- and saline-treated mice. However, there was a 23% and 29% ($p<0.01$) decrease in platelets in TAT-BH3 peptide as compared to saline- and TAT-inactive BH3 peptide-treated arthritic mice, respectively (Table 2). These data indicate that TAT BH3-peptide treatment is relatively non-toxic in the K/BxN model of inflammatory arthritis.

TABLE 2

| (1E6) | Saline | TAT-BH3-inactive | TAT-BH3 |
|---|---|---|---|
| B-cells+ | 2.19 ± 0.11 | 2.38 ± 0.21 | 2.51 ± 0.11 |
| T-cells | 2.31 ± 0.08 | 1.94 ± 0.17 | 2.20 ± 0.10 |
| CD4+ T-cells | 1.31 ± 0.05 | 1.15 ± 0.10 | 1.25 ± 0.06 |
| CD8+ T-cells | 0.91 ± 0.04 | 0.72 ± 0.06 | 0.86 ± 0.04 |
| Resident Monocytes | 0.16 ± 0.02 | 0.14 ± 0.01 | 0.21 ± 0.02" |
| Inflammatory monocytes | 0.32 ± 0.07 | 0.25 ± 0.03 | 0.26 ± 0.03 |
| N-K-cells | 0.29 ± 0.03 | 0.19 ± 0.13 | 0.23 ± 0.02 |
| Total Leukocytes | 6.43 ± 0.34 | 6.1 ± 0.18 | 6.2 ± 0.22 |
| Platelets | 1205.75 ± 20.0 | 1305.75 ± 70.03 | 930.3 ± 55.32* |
| RBCs | 9.04 ± 0.26 | 9.84 ± 0.22 | 9.60 ± 0.42 |

Peripheral blood was isolated by cardiac sticks. Cells were blocked for 10 minutes with Fc block and then stained with anti-CD45, anti-CD19, anti-CD3, anti-CD4, anti-CD5, anti-CD11b, anti-Gr-1, and anti-CD62L antibodies for 30 minutes. Platelets and RBCs were determined on an automated hematology analyzer ABX Pentra 60. Following incubation with antibodies red blood cells were lysed and cells were fixed with Becton Dickenson FACS lysing solution. Values represent the mean±standard error, which were compared by Student's t-test. * denotes $p<0.05$ as compared to saline and TAT-BH3 inactive peptides under parallel conditions.

Figure 5:
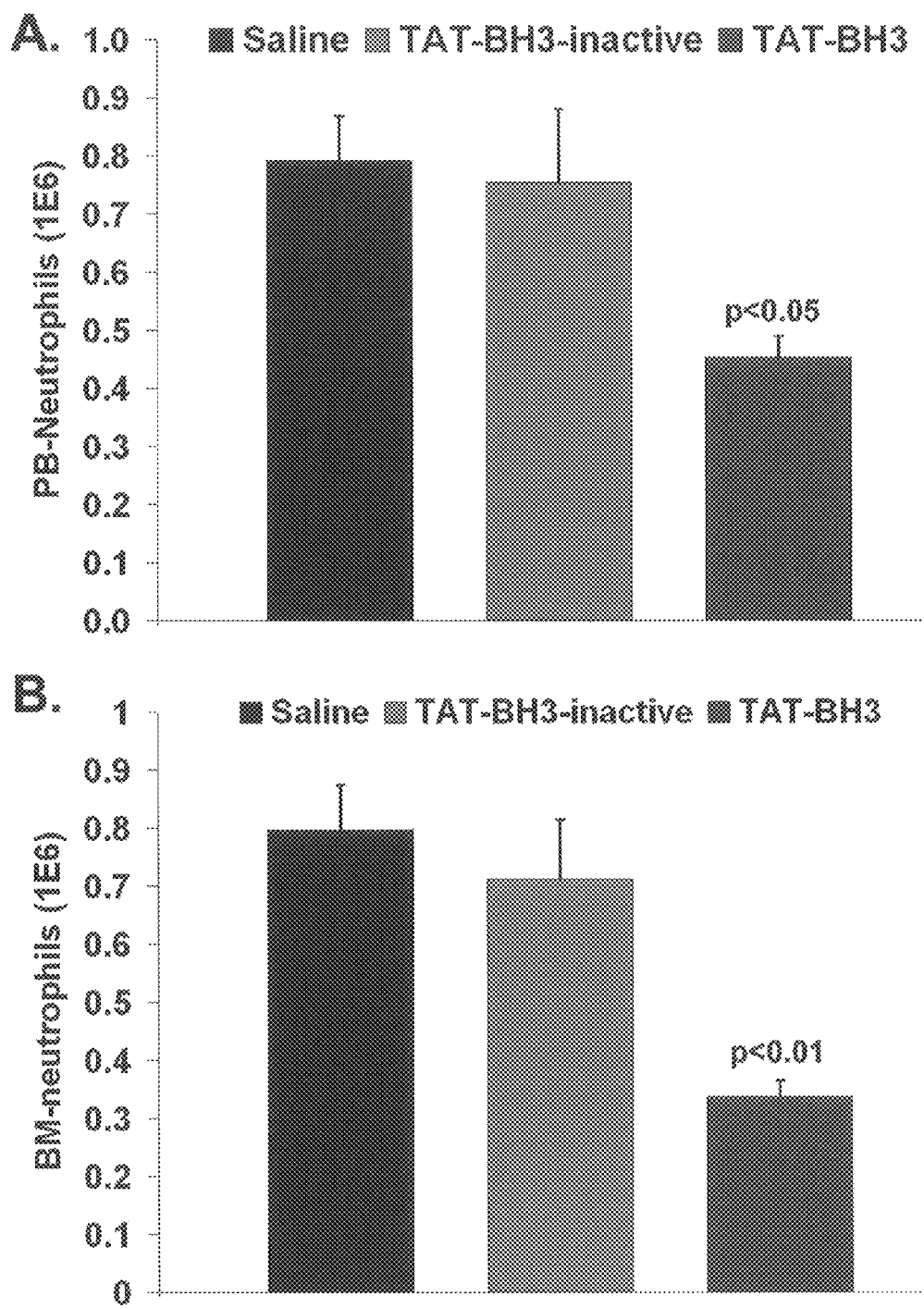
FIG. 5A is a representative bar chart showing reduced numbers of peripheral blood neutrophils in BH3 peptide treated mice.
FIG. 5B is a representative bar chart showing a reduction in neutrophil bone marrow population in BH3 peptide treated mice.

TAT-BH3 peptides decrease the number of neutrophils in circulation and in bone marrow. We have shown that numbers of neutrophils and macrophages are reduced in the joints of mice treated with TAT-BH3 peptides. Analysis of peripheral blood from saline-, TAT-inactive BH3 peptide, and TAT-BH3-treated arthritic mice revealed no decrease in any of the sub-populations circulating in blood (Table 2) except for neutrophils. There was a 40% ($p<0.05$) decrease in the numbers of neutrophils in TAT-BH3 peptide-treated mice as compared TAT-inactive peptide, and saline-treated mice (FIG. 5A). This decrease in numbers of peripheral blood neutrophil in TAT-BH3 peptide-treated mice was associated with a 50% ($p<0.03$) decrease in the numbers of mature neutrophils in bone marrow as compared saline- and TAT-inactive BH3 peptide-treated mice (FIG. 5B). Taken together, the data suggests that TAT-BH3 peptides suppress the development of arthritis by limiting the neutrophils response.

The various embodiments of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention. The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A method of treating an immune-mediated disease in a patient comprising the step of:
    administering a pharmaceutical composition to said patient in need thereof, said composition including a cell delivery agent that is a cell-penetrating peptide selected from the group consisting of TAT, penetratin, VP22, transportan, synthetic oligoarginines, and combinations thereof that is conjugated to a cell death agent that is the BH3 domain of Bim, in an amount sufficient to provide a clinically observable improvement in the disease symptoms of said patient;
    wherein said immune-mediated disease is selected from the group consisting of rheumatoid arthritis and juvenile polyarticular rheumatoid arthritis.

2. The method of claim 1 wherein said patient is a human.

3. The method of claim 1 wherein said patient is an animal.

4. The method of claim 1 wherein said administering step is selected from the group consisting of intraperitoneal, intrarteriole, intramuscular, interdermal, subcutaneous, perenteral and intraventricular.

5. The method of claim 1 wherein said amount is about 0.1-10 mg/kg per day.

6. The method of claim 1 wherein said composition is dispersed in a pharmaceutically acceptable carrier.

7. The method of claim 1 composition suppresses the number of neutrophils in said patient.

8. The method of claim 1 where the immune-mediated disease is rheumatoid arthritis.

9. The method of claim 1 where the cell delivery agent conjugated to the BH3 domain of Bim is the polypeptide of SEQ ID:1 and the immune-mediated disease is rheumatoid arthritis.

* * * * *

UNITED STATES PATENT AND TRADEMARK OFFICE
CERTIFICATE OF CORRECTION

PATENT NO.       : 8,785,388 B2  
APPLICATION NO.  : 12/031118  
DATED            : July 22, 2014  
INVENTOR(S)      : Harris R. Perlman Page 1 of 1

It is certified that error appears in the above-identified patent and that said Letters Patent is hereby corrected as shown below:

In the Claims

In Col. 18, line 29, Claim 7, after the term claim 1 insert -- wherein said --

Signed and Sealed this  
Twenty-fifth Day of November, 2014

Michelle K. Lee  
*Deputy Director of the United States Patent and Trademark Office*

SEQUENCE LISTING

```
<160> NUMBER OF SEQ ID NOS: 2

<210> SEQ ID NO 1
<211> LENGTH: 32
<212> TYPE: PRT
<213> ORGANISM: Homo sapiens
<220> FEATURE:
<221> NAME/KEY: X
<222> LOCATION: (1)..(1)
<223> OTHER INFORMATION: Ac
<220> FEATURE:
<221> NAME/KEY: X
<222> LOCATION: (7)..(7)
<223> OTHER INFORMATION: Orn
<220> FEATURE:
<221> NAME/KEY: X
<222> LOCATION: (32)..(32)
<223> OTHER INFORMATION: OH

<400> SEQUENCE: 1

Xaa Arg Lys Lys Arg Arg Xaa Arg Arg Glu Ile Trp Ile Ala Gln
1               5                   10                  15

Glu Leu Arg Arg Ile Gly Asp Glu Phe Asn Ala Tyr Tyr Ala Arg Xaa
            20                  25                  30

<210> SEQ ID NO 2
<211> LENGTH: 32
<212> TYPE: PRT
<213> ORGANISM: Homo sapiens
```

```
-continued

<220> FEATURE:
<221> NAME/KEY: X
<222> LOCATION: (1)..(1)
<223> OTHER INFORMATION: Ac
<220> FEATURE:
<221> NAME/KEY: X
<222> LOCATION: (7)..(7)
<223> OTHER INFORMATION: Orn
<220> FEATURE:
<221> NAME/KEY: XX
<222> LOCATION: (32)..(32)
<223> OTHER INFORMATION: OH

<400> SEQUENCE: 2

Xaa Arg Lys Lys Arg Arg Xaa Arg Arg Arg Glu Ile Trp Ile Ala Gln
1               5                   10                  15

Glu Ala Arg Arg Ile Gly Ala Glu Phe Asn Ala Tyr Tyr Ala Arg Xaa
            20                  25                  30
```